United States Patent [19]

Davidson

[11] Patent Number: Plant 7,729

[45] Date of Patent: Dec. 3, 1991

[54] ROSE PLANT: 'SMOOTH MELODY'

[76] Inventor: Harvey D. Davidson, #3 El Verano Rd., Orinda, Calif. 94563

[21] Appl. No.: 583,955

[22] Filed: Sep. 17, 1990

[51] Int. Cl.[5] ..... A01H 5/00

[52] U.S. Cl. ..... Plt./22

[58] Field of Search ..... Plt./1, 2, 12, 13, 22, Plt./23, 27

*Primary Examiner*—Howard J. Locker

[57] ABSTRACT

A new rose variety of the Floribunda class characterized by having clusters of medium-sized red and white flowers on a thornless bush with disease resistant glossy foliage.

1 Drawing Sheet

1

The present invention relates to a new and distinctive variety of rose plant of the Floribunda class, which was originated by my crossing 'Royal Flush' as the seed parent with 'Smooth Lady' (U.S. Plant Pat. No. 6,147) as the pollen parent.

Among the novel characteristics possessed by the new variety which distinguish it from:

(a) Its parents and all other varieties of which I am aware are:
  (1) A plant which is thornless throughout.
  (2) A bicolor flower of red with various patterned inner white shadings; having white outside petals with red edge; the flower aging to red on inside of petals.
  (3) Very rapid flowering cycles.
  (4) Good keeping quality as a cut flower.
  (5) A vigorous upright plant of medium height.

(b)
  *Seed parent.*—Hybrid tea, cream with pink edges, semi-thornless.
  *Pollen parent.*—Hybrid tea, pink, very tall.

Asexual reproduction of the new rose variety by budding, as performed at Tulare, Calif. shows that the aforementioned characteristics and distinctions come true to form and are established and transmitted through succeeding propagations.

The accompanying drawing shows typical specimens of the vegetative growth and flower of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

American Rose Society Registration commercial appellation: 'Smooth Melody.'

Parentage: Seedling.
  *Seed parent.*—'Royal Flush.'
  *Pollen parent.*—'Smooth Lady.'

Class: Floribunda.

2

The following observations are made of specimens grown outdoors in Contra Costa County, Calif., in the month of September.

FLOWER

Blooming Habit

A. Bud:
  (1) *Size.*—Medium.
  (2) *Form.*—Ovoid and pointed.
  (3) *Sepals.*—To 22 mm in length; having 8 mm extension beyond bud. No serration shown on sepal edges. Generally 2 out of 5 sepals show 2 appendages on each side of 1 to 3 mm length; very light cotton matting on inner surface of sepals. Light hairs on outer surface. Color before breaking — 144B; when turned down — 147C.
  (4) *Peduncle.*—Length — 4 cm; Surface — smooth, no prickles of hairs; Strength — stiff, slight curvature. Color — 144B flushed 172B.
  (5) *Color.*—When sepals first divide — outside petals 57B, shading to 57C; areas lastly covered by sepals are close to 4C.

B. Bloom:
  (1) *Size.*—Average when open — 8½ cm.
  (2) *Borne.*—Usually cluster of 3 to 4; Occasional single.
  (3) *Form.*—Cupped; rapid open; flat when fully open at maturity.
  (4) *Petalage.*—Average number — 26.
  (5) *Color.*—Early open — inside surface; from outer edge for 2 cm: 57C shading then 57D to 58C. From center 1.5 cm white, irregular design with slight veining of 57D. Surface aging to 57B. Outside surface: white with outer edge of 57B. Aging: 57C developing in white area.

C. Petals:
  (1) *Texture.*—Thick.
  (2) *Appearance.*—Satiny on both inside and outside.
  (3) *Form.*—Round, tapering toward base. Edge with pointed center.
  (4) *Arrangement.*—Regular at all stages, slightly ruffled appearance.
  (5) *Petaloids in center.*—Average 4 to 6.
  (6) *Persistence.*—Drop off cleanly.
  (7) *Fragrance.*—Strong fruit.
  (8) *Lasting quality.*—Moderate on bush; good cut flower.

REPRODUCTIVE ORGANS

A. Stamen:

(1) *Arrangement.*—Regularly arranged around styles.

(2) *Number.*—Average 13 94 to 98.

(3) *Length.*—Average — 5 to 10 mm.

(4) *Filaments.*—Color — 57D.

(5) *Anthers.*—Color — 21A.

(6) *Pollen.*—21D.

B. Pistil:

(1) *Styles.*—Covered with fine white hairs at base; color: 159D.

(2) *Stigma.*—Color — Close to 159B.

(3) *Ovary.*—Rounded, 8 mm through center diameter.

C. Hips: Readily accepts own pollen, rarely accepts foreign pollen.

(1) *Shape.*—Rounded; to 1½ cm diameter, to 1½ cm depth.

(2) *Color.*—When mature near 33B.

(3) *Seed.*—Average 15 to 20, frequently exposed.

PLANT

A. Form: Upright.

B. Growth: Vigorous; medium height — average 1.0 meters.

C. Foliage: Compound of 3 to 5 leaflets on bloom stem; 5 to 7 leaflets on main canes.

(1) *Size.*—Large.

(2) *Quantity.*—Stems well covered.

(3) *Color.*—New foliage upper side — 176A, under side — 176A with green veining. Old foliage — upper side 147A, under side — 147B.

(4) *Shape.*—Oval with center pointed.

(5) *Texture.*—Upper side — leathery, glossy. Under side — smooth, dull.

(6) *Edge.*—Slight serration on outer edge. Average points 4 per 1 cm, with up to 1 mm peak.

(7) *Rachis.*—Slight glandular hair on upper side; lower side occassional 3 to 4 hooked 1 mm prickles about 2 mm spacing.

(8) *Stipules.*—Average length 2.5 cm.; Auricle to 6 mm.

d. Resistance to disease: Mildew, rust and blackspot — very good.

E. Wood:

*New wood.*—Color near 183B, Bark — smooth.

*Old wood.*—Color near 144B, Bark — smooth.

F. Thorns: None.

G. Winter hardiness: Good.

I claim:

1. A new and distinct thornless variety of rose plant of the Floribunda class, substantially as herein shown and described.

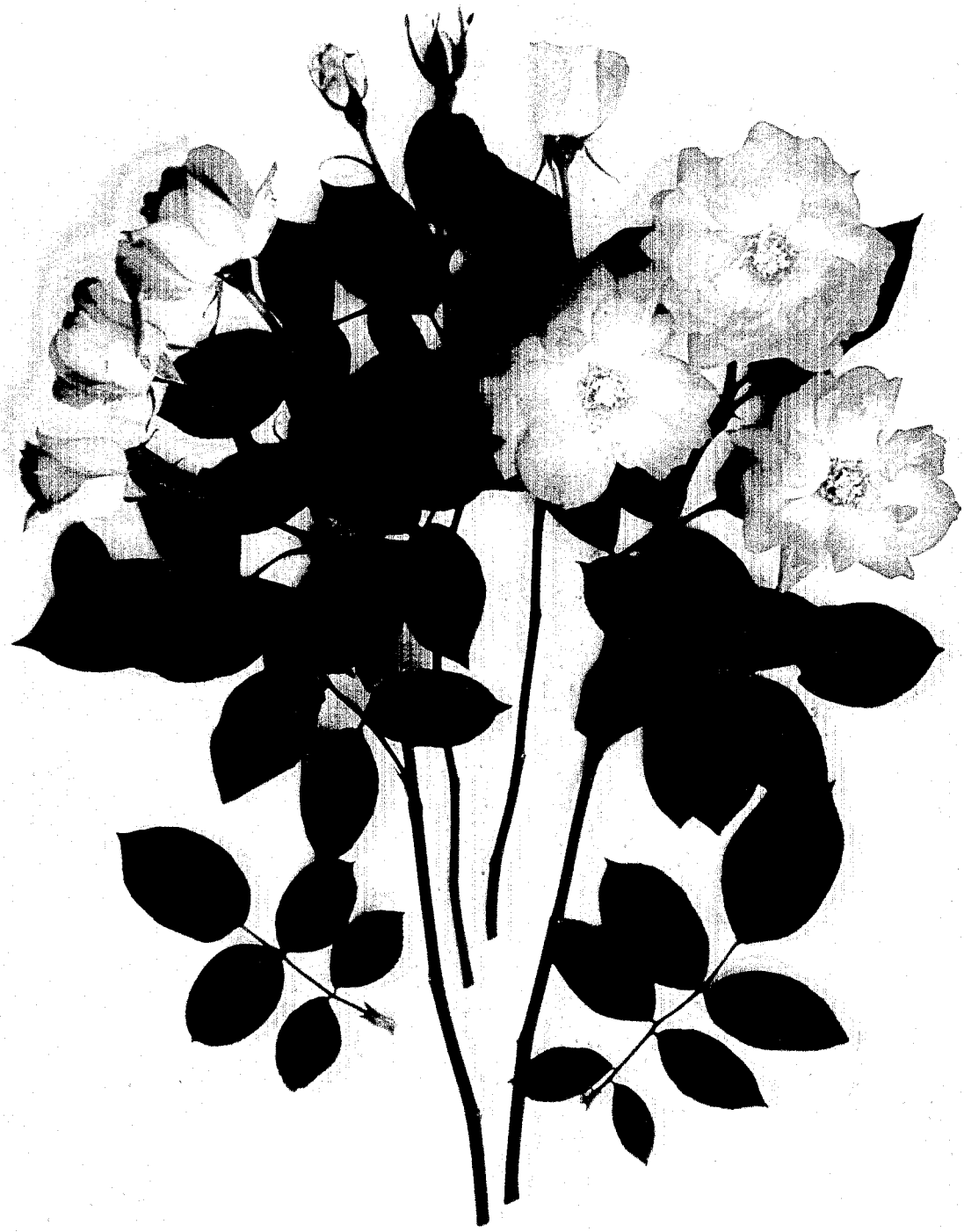

* * * * *